United States Patent [19]
Campbell et al.

[11] Patent Number: 6,120,479
[45] Date of Patent: Sep. 19, 2000

[54] AUTO-DESTRUCT DISPOSABLE SYRINGE

[76] Inventors: Douglas C. V. Campbell, Suite 202-203, 190 Colonade Road, Ottawa, ON, Canada, K2E 7J5; Peter Frise, 4464 Hunt Club CR., Windsor, Ontario, Canada, N9G 2P6; Frank Johnson, 169 Fifth Avenue, Ottawa, Ontario, Canada, K1S 2M8

[21] Appl. No.: 09/123,141

[22] Filed: Jul. 27, 1998

Related U.S. Application Data

[63] Continuation of application No. PCT/CA97/00066, Jan. 24, 1997.

[30] Foreign Application Priority Data

Jul. 27, 1997 [CA] Canada .................................. 2168201

[51] Int. Cl.⁷ ...................................................... A61M 5/00
[52] U.S. Cl. ............................ 604/110; 604/111; 604/228
[58] Field of Search ............................ 604/110, 93, 181, 604/187, 208, 218, 228, 111, 219

[56] References Cited

FOREIGN PATENT DOCUMENTS

1727846-A1   2/1990   U.S.S.R. ................................ 604/187

*Primary Examiner*—Ronald Stright
*Assistant Examiner*—Jeremy Thissell
*Attorney, Agent, or Firm*—Rader, Fishman & Grauer, PLLC

[57] ABSTRACT

A disposable auto-destruct syringe is disclosed which includes a syringe barrel for holding an injectable fluid, a piston reciprocatable in the barrel and sealingly engaging the barrel wall, a plunger having a forward portion normally positioned in the barrel and a rearward portion to be manipulated by a user of the syringe, a coupling mechanism for connecting the piston with the plunger to permit axial movement of the piston in the barrel by operation of the plunger, and a deforming structure for permanently deforming the barrel wall to break the seal between the piston and the barrel wall. The deforming structure is in the form of cutters or burrowing elements mounted by-way of elastic arms to one of the piston and the plunger. The deforming structure is movable from an at rest position wherein the barrel wall is not deformed, to a barrel wall engaging position wherein the barrel wall is permanently deformed by the deforming structure. The syringe further includes an engaging mechanism for forcing the deforming structure into the barrel wall engaging position upon rearward movement of the piston after a full or partial injection stroke only. The engaging mechanism is mounted to the other of the piston and plunger. This construction provides for an auto-destruct syringe wherein the barrel wall is permanently deformed not during the injection stroke, but only when refilling of the syringe is attempted after a full or partial injection stroke so that the auto-destruction action does no longer interfere with the injection stroke.

10 Claims, 3 Drawing Sheets

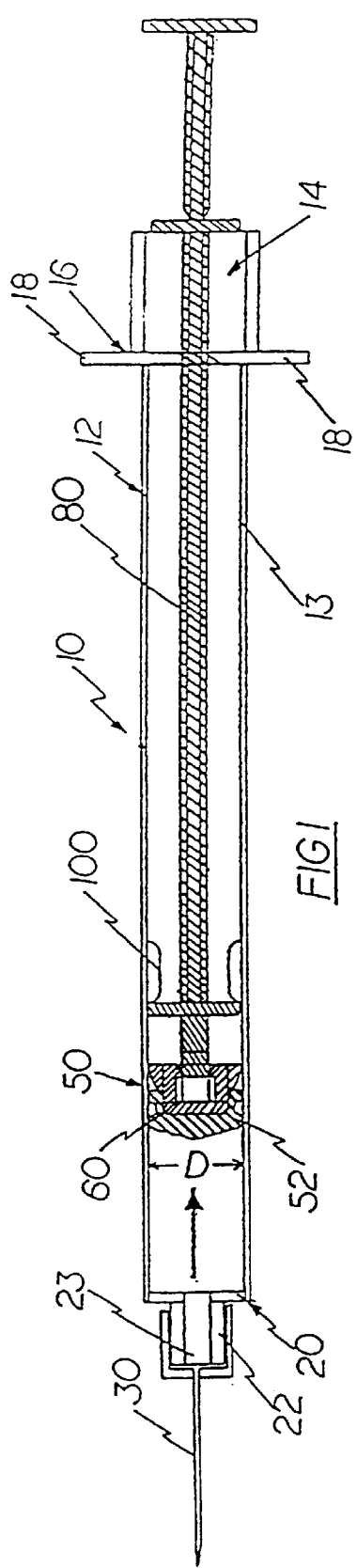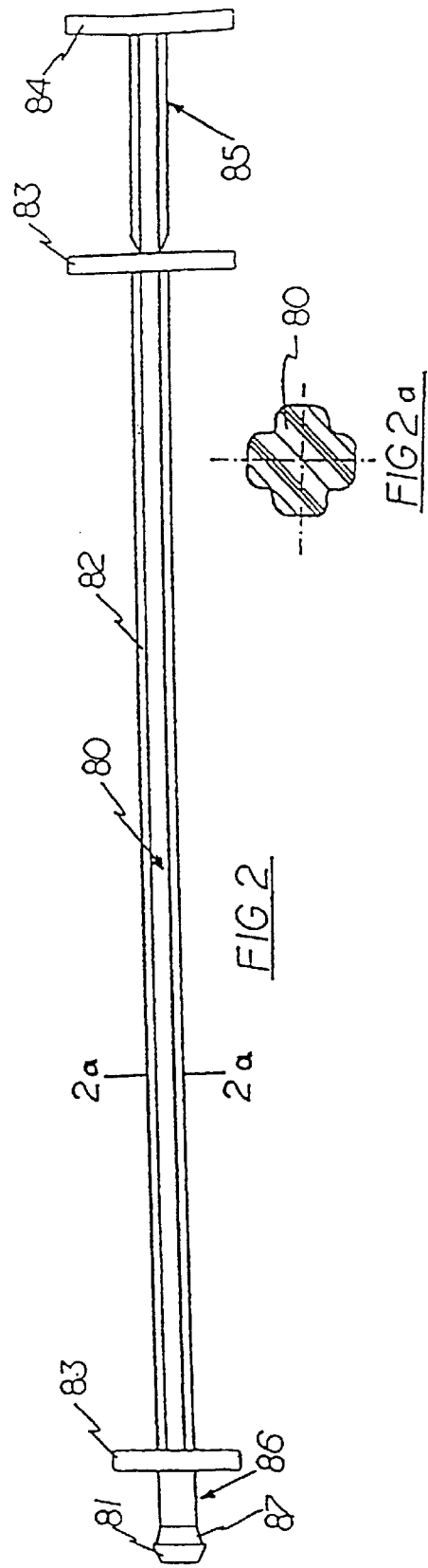

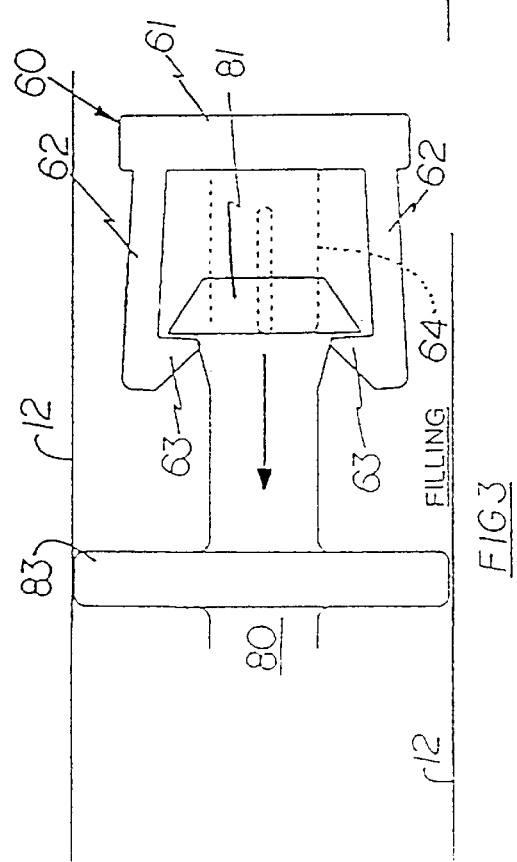
FIG 3 FILLING
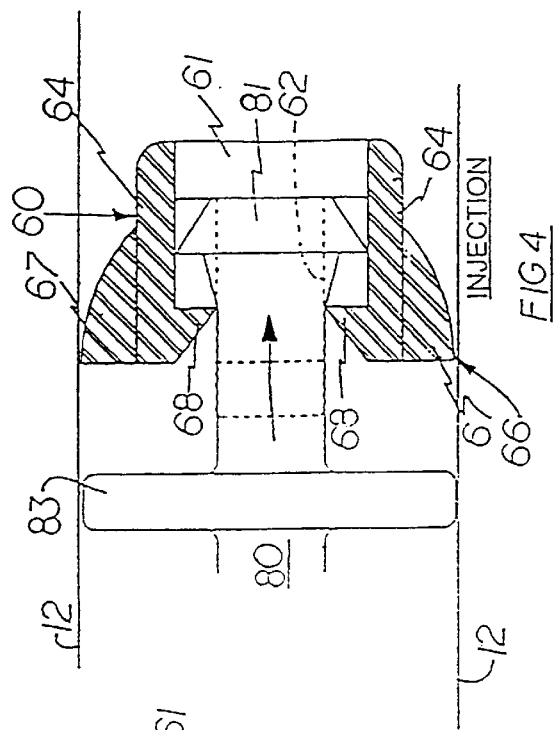
FIG 4 INJECTION
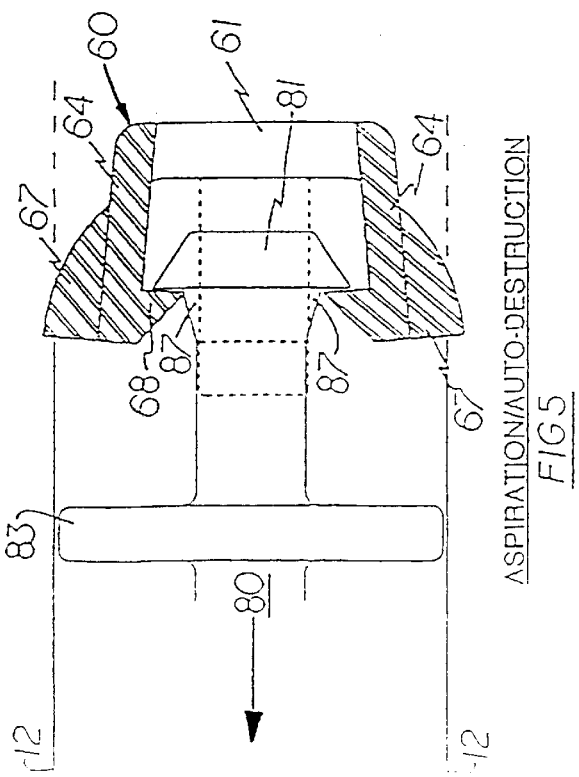
FIG 5 ASPIRATION/AUTO-DESTRUCTION
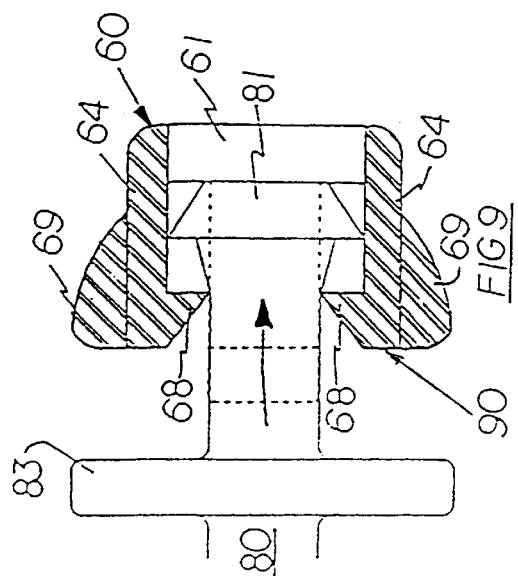
FIG 9

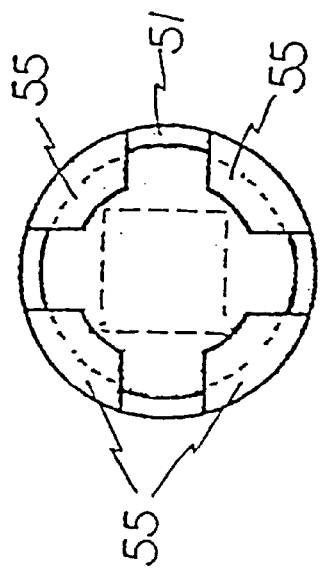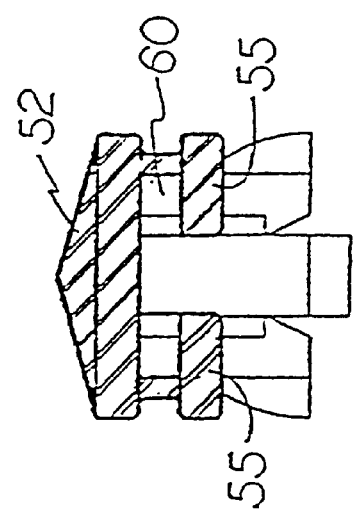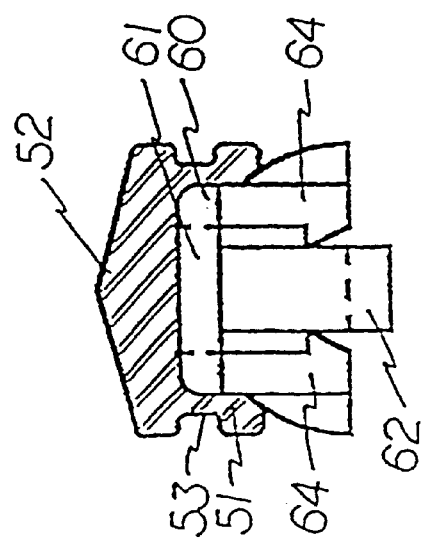

AUTO-DESTRUCT DISPOSABLE SYRINGE

BACKGROUND OF THE INVENTION

This invention is a continuation of International Patent Application No. PCT/CA97/00066, filed on Jan. 24, 1997.

Field of the Invention

SUMMARY OF THE INVENTION

Communicable diseases are transmitted in different ways, for example, by contact with body fluids of an infected person. Infection with a communicable disease is undesired and is especially unfortunate when due to inadvertence or ignorance such as when caused by the sharing or reuse of hypodermic syringes. The practice of sharing and/or reusing, hypodermic syringes is especially prevalent among drug users and in third world countries where syringes are used in vaccination campaigns. Often several children are inoculated with the same syringe either by using large capacity syringes for multiple small injections, or by refilling and reusing the syringes after insufficient sterilization. As a result potentially disastrous, body fluid transmitted diseases, especially AIDS and Hepatitis have spread at an alarming rate among drug users and in third world countries, and they are particularly among children. Although not all new cases are attributable to syringe reuse or sharing, it is estimated by the World Health Organization that the total number of new cases could be significantly reduced if transmission through contaminated syringes were prevented. In an effort to frustrate the reuse of hypodermic syringes, disposable syringes have been developed which are intended to operate only for one single injection.

Various single-use syringe constructions are known in the art, which can be grouped into three basic categories; the piston or plunger lock type, wherein retraction of the piston is prevented either always or after completion of the injection; the plunger separating type, wherein the plunger separates from the piston or the piston seal when the plunger is retracted; and the cutting type wherein the barrel wall is cut during injection. It is a major disadvantage that in the first two types of single-use syringes the barrel which is the most important part of any functioning syringe remains intact and may be tampered with and reused. Thus, single-use syringes wherein the barrel is rendered unusable, for example through cutting of the barrel wall, are preferable. However, the cutting type syringes also have certain disadvantages.

Chiquar-Arias in U.S. Pat. No. 3,667,657 disclose prefilled syringes which include a small stationary knife that is laterally fixed to the syringe plunger and engages an opening in the wall of the syringe barrel. When the plunger is forced down into the barrel, as during injection, the barrel wall is cut. This destroys the barrel behind the piston seal and makes reuse of the syringe impossible. However, it is a disadvantage of prefilled syringes that they can only be used in those circumstances where injection of the respectively included liquid is desired. In other words, numerous syringes filled with different inoculants are required which increases manufacturing and storage costs.

In U.S. Pat. No. 3,951,146 Chiquar-Arias describe syringes wherein the plunger includes a housing or recess for a small knife which is forced radially outwardly by a spring. The knife has a rounded rear edge and a forward cutting edge. The plunger can be moved backward for filing of the syringe without cutting or damaging the barrel wall. For insertion of the plunger, a protection strip is inserted between the knife and the barrel wall, which strip is then removed. Use of the protection strip is disadvantageous, since it adds an additional manufacturing step and, thus, increases production cost. Furthermore, the spring loaded knife stays in contact with the barrel wall at all times, which, despite the rounded rear edge of the knife, could damage the barrel wall during aspiration of the inoccularit and lead to leakage around the plunger or through the barrel wall.

An auto-destruct disposable syringe with retractable knives is disclosed in Canadian Patent Application SN. 2,045,499 by Fenet. The syringe includes a barrel, a piston, and a plunger for moving the piston axially in the plunger. The knives are mounted on flexible arms which are connected with the plunger and are retracted during the aspiration stroke of the syringe. When the aspirated liquid is expelled from the barrel during injection, the plunger is pushed against the piston which moves the free end of the arms along a ramp on the piston. This forces the knives against the barrel wall. The plunger and, thus, the knives are oriented to be opposite preselected areas of reduced thickness in the barrel wall. The reduced wall thickness permits penetration of the knives and cutting of the barrel wall, thereby destroying the barrel behind the piston as it is forced into the barrel during injection. As a result, the syringe cannot be reused, since the barrel will no longer hold a vacuum and any liquid contained therein will leak through the cut areas of the barrel wall.

It is a disadvantage of this syringe construction that the auto-destruct mechanism thereof can be rendered useless by rotating the plunger in the barrel until the knives can no longer engage the weakened areas in the barrel wall during injection. Furthermore, if the barrel wall in the weakened areas is too thin, barrel integrity may be compromised resulting in a bursting of the barrel during injection. On the other hand, if the wall thickness in the weakened areas is too large, the cumulative force required for moving the piston down the barrel and simultaneously cutting the barrel wall during injection may become excessively large. This may render the syringe impractical. It also may result in rejection of the syringe under national and/or international regulations which, for example, require that a maximum axial force required for pushing the piston down the barrel during injection not be exceeded. Moreover, since auto-destruct syringes must be discarded after a single use, they should be made available at the lowest possible price to reduce the financial strain on the patient, the health care system and international health organizations. This requires that the syringe be manufactured from relatively economical materials such as plastics. However, during tests with knives manufactured from plastics material, the inventors of the present application have found that knives made from inexpensive plastics tend to quickly become blunt. This may lead to failure of the knives part way during the injection stroke leaving the front portion of the barrel intake and allowing partial reuse of the syringe. Thus, an economical auto-destruct syringe is desired which reliably prevents even partial reuse.

German published application DE 4 034 673 of Bader discloses an auto-destruct syringe wherein either the barrel wall is cut during the injection stroke or the piston is locked in the barrel after injection or the plunger separated from the piston after full or partial injection when a second aspiration of the syringe is attempted. As far as the cutting during injection is concerned, this disclosed structure is subject to the same problems as the one of Fenet. Furthermore, separation of the plunger from the piston cannot guarantee that the syringe barrel is not reused with a new plunger/piston combination. Only destruction of the barrel reliably prevents reuse of a syringe. Bader further discloses a syringe construction whereby the syringe barrel is destroyed only on an attempt to refill the syringe after a full or partial injection stroke. However, this can only be achieved by using an additional part. A protection cap is used which covers the cutting or scoring elements of the syringe during the initial aspiration stroke. This is disadvantageous since it requires the manufacture of a separate, additional part which increases manufacturing, storage and assembly costs.

SUMMARY OF THE INVENTION

Accordingly, the invention provides an auto-destruct syringe comprising a syringe barrel for holding a fluid having an open rear end and a closed front end and a passage extending through the closed front end to permit expulsion of fluid from the interior of the barrel;

a piston reciprocatable in the barrel and sealingly engaging the barrel wall;

a plunger having a forward portion normally positioned in the barrel and a rearward portion to be manipulated by a user of the syringe;

coupling means for connecting the piston with the plunger to permit axial movement of the piston in the barrel by operation of the plunger;

deforming means for permanently deforming the barrel wall to brake the seal between the piston and the barrel wall, the deforming means being mounted to one of the piston and the plunger and movable from an at rest position wherein the barrel wall is not deformed by the deforming means, to a barrel wall engaging position wherein the barrel wall is permanently deformed by the deforming means; and engaging means for forcing the deforming means into the barrel wall engaging position upon rearward movement of the piston after a full or partial injection stroke, the engaging means being mounted to the other end of the piston and plunger.

The term permanently deforming the barrel wall in the context of this application is intended to include puncturing or cutting of the barrel wall, burrowing into the side wall to produce a permanent groove, and other actions which will break the seal between the piston and the barrel wall and allow leakage around the piston, thereby preventing the generation of pressure or vacuum in the barrel.

BRIEF DESCRIPTION OF THE DRAWINGS

In the drawings:

Preferred embodiments of the invention will now be further described by way of example only and with reference to the attached drawings, wherein FIG. 1 is an axial cross-section of a preferred embodiment of the auto-destruct syringe in accordance with the invention;

FIG. 2 is an enlarged side view of the plunger of the embodiment shown in FIG. 1;

FIG. 2a is a cross-section through the plunger shown in FIG. 2 taken along line 2a—2a;

FIG. 3 is an axial cross-section taken along the plane of FIGS. 1 and 2 through the piston/plunger combination of the preferred embodiment shown in FIG. 1 during the first aspiration stroke;

FIG. 4 is an axial cross-section through the piston/plunger combination shown in FIG. 3 but taken along a plane orthogonal to the plane of FIG. 3 and illustrating the combination during the injection stroke;

FIG. 5 illustrates the piston/plunger combination shown in FIG. 4 but during the second aspiration stroke;

FIG. 6 is an axial cross-section through the piston/stopper combination of the embodiment shown in FIG. 1;

FIG. 7 is a rear end view of the piston seal of the embodiment shown in FIG. 1;

FIG. 8 is a cross-section through the piston/stopper combination 50 taken along a plane rotated 45° from the one of FIG. 6; and FIG. 9 illustrates the piston/plunger combination shown in FIG. 5 but with deforming elements which have blunt edges and burrow into the barrel wall instead of cutting it.

DETAILED DESCRIPTION

The preferred embodiment of an auto-destruct disposable syringe in accordance with the invention is packaged in the empty condition and allows aspiration of an injectable liquid prior to injection. The syringe includes a mechanism which breaks the seal between the piston of the syringe and the syringe barrel when reuse is attempted after full or partial injection.

In general, a syringe in accordance with the invention as shown in FIG. 1 of the drawings consists of a syringe body 10 including a barrel 12, a piston assembly 50 including a piston 60 and an auto-destruct mechanism for permanent deformation of the barrel wall 13, a plunger 80 and a coupling mechanism connecting the plunger 80 with the piston 50 thereby allowing the user of the syringe to reciprocate the piston by way of the plunger.

The syringe body 10 consists of the cylindrical barrel 12 which has an open rear end 14 and a closed front end 20. A collar 16 is provided at the rear end 14 which includes a pair of diametrically opposite wings 18 that provide finger rests during aspiration and injection. The front end 20 of the barrel is provided with an integral needle mount 22 for attachment of a hypodermic needle 30. The front end 20 further has a fluid passage 23 for the expulsion of fluid from the barrel interior and into the needle 30. Although the needle 30 can be removably attached to the mount 22 for separate disposal, it is preferably permanently affixed to the needle mount 22 to prevent the reuse of possibly contaminated needles with new syringes.

The piston assembly 50 includes a substantially cup-shaped piston seal or stopper 52 which is made of elastomeric seal material such as butyl rubber used in conventional syringe piston seals. Although use of a piston seal in the form of a separate stopper is preferred, it is known in the art that a satisfactory seal between the piston and the barrel wall can be achieved without separate stoppers, i.e. by seals integrated into the piston or by tight engagement between the piston and the barrel wall. The stopper 52 is connected with piston 60 by way of an interference fit (see FIGS. 6–8). The cylindrical sidewall 51 of the stopper 52 has an outer diameter which is slightly larger than the inner diameter D of the barrel 12 to ensure a liquid tight sliding engagement therebetween. A circumferential groove 53 is provided in the outer surface of the stopper sidewall 51 to improve the sealing characteristics of the stopper. In the alternative, the stopper can have a diameter which is marginally smaller than the barrel diameter D and include one or more circumferential sealing ribs giving the stopper an overall diameter larger than D thereby ensuring a reliable seal. At the piston engaging end, the stopper sidewall 51 is provided with four circumferentially equally spaced, radially inwardly projecting flaps 55 which are integral with the sidewall 51 and extend between the drag/carrier arms of the piston that will be described in more detail in the following.

The piston 60 (see FIGS. 3–5) has a cylindrical base 61 which snugly fits into the stopper 52 and two pairs of arms extending from the base in rearward direction. A pair of diametrically opposed axially extending drag arms 62 form a coupling mechanism for connecting the piston 60 with the plunger 80. To this end, each drag arm has a hook-shaped rear end 63 for engagement with an enlarged, mushroom shaped head 81 on the forward end 86 of the plunger 80. This provides a coupling mechanism which allows the piston 60 to be moved rearward in the barrel 12 by pulling back the plunger 80 during the initial aspiration stroke. The plunger 80 (see FIGS. 2 and 2a) has a shaft 82 of substantially square cross-section and guide plates 83 integral with the shaft 82 to center the shaft in the barrel. A thumb plate 84 is integrally molded onto a rear end 85 of the shaft, while the forward end 86 of the plunger, which end normally extends into the barrel 12, includes the mushroom-shaped head 81 for engagement by the hook-shaped ends 63 of the drag arms 62. The shaft front end is further provided with a frustoconical forwardly inclined ramp portion 87 which is located behind head 81 and forms part of a barrel wall deforming mechanism 90 of the syringe.

The barrel wall deforming mechanism 90 provides for permanent deformation of the barrel wall 12 when an attempt is made to refill the syringe. This breaks the seal between the stopper 52 and the barrel wall, which renders the syringe useless. The deforming mechanism consists of a pair of diametrically opposed axially extending flexible carrier arms 64 connected to and extending rearward from the piston base 61. The carrier arms 64 and the drag arms 62 are alternately positioned and circumferentially evenly spaced about the center of the piston base 61. The carrier arms 64 respectively include at their free end a radially outwardly protruding integral mechanism. Furthermore, the coupling mechanism and the deforming mechanism can be combined into a single structure, for example, by mounting the hook portions 68 and the deforming elements 66 on the drag arms.

The drag arms 62 in the preferred embodiment are longer than the carrier arms 64. The hook-shaped ends 63 of the drag arms 62, the head 81 of the shaft, the ramp portion 87 and the hook portions 68 of the carrier arms 64 respectively are dimensioned such that when the plunger is inserted into the piston until the hook-shaped ends 63 engage behind the head 81, the hook portions 68 and ramp portion 87 are axially spaced apart. Furthermore, the drag arms 62 are shaped such that the hook-shaped ends 63 thereof are normally radially spaced apart from the barrel wall. The spacing is selected such that the drag arms 62 do not engage the barrel wall when the mushroom-shaped head-81 of the plunger 80 is positioned therebetween during assembly of the syringe. It will be apparent from the above description and the attached drawings that the stopper 52 extends rearward around the piston 60, or in other words the piston is recessed into the stopper in the preferred embodiment. As a result, the deforming elements 66 are located closely adjacent the seal line between the stopper 52 and the barrel wall 12 so that substantially no portion of the barrel wall will remain intact when refilling of the syringe is attempted after injection.

The piston 60 with the drag and carrier arms 62, 64 and the plunger 80 are each preferably integrally extrusion molded from an extrudable, thermoplastic material, preferably polypropylene.

Although in the above described arrangement of the coupling and deforming mechanisms is preferred, it will be readily apparent that the location of the drag arms 62 and the mushroom shaped head 81 on the piston 60 and plunger 80 respectively can be exchanged without having an effect on the function of the syringe of the invention. Equally, the positions of the carrier arms 64 with the deforming elements 66 and of the ramp portion 87 may be exchanged so that the carrier arms are affixed to the plunger 80 and the ramp portion is provided on the piston 60.

To facilitate permanent deformation of the barrel wall, the thickness of the barrel wall can be reduced along diametrically opposite grooves as known in the art from the self-destruct syringe disclosed by Fenet in Canadian Patent Application SN 2,045,499. If the barrel wall is provided with such grooves, the rotational position of the carrier arms 64 in the barrel must be controlled to ensure reliable engagement of the deforming elements 66 with the grooves. Furthermore, it may be possible to render the syringe reusable by rotating the piston 60 in the barrel until the deforming elements 66 are no longer opposite one of the grooves. In order to prevent this, the barrel wall in the preferred embodiment is made evenly thin along its whole circumference so that rotation of the piston 66 in the barrel no longer has any effect on the function of the deforming elements. Furthermore, in the most preferred embodiment the deforming elements 66 are burrowing elements 67 which have a blunt radially outer edge 69 that does not cut the barrel wall but simply burrows into the barrel wall to create a permanent groove which permits air to pass around the plunger. Consequently, reuse of the syringe is made impossible, since the barrel will no longer hold the vacuum required for refilling of the syringe. Moreover, when the barrel wall is made evenly thin, permanent deformation of the barrel wall by the deforming elements may be carried out either during the injection or the second aspiration stroke. The barrel wall is preferably of a thickness of 0.01 to 0.2 mm and extrusion molded of a substantially rigid thermoplastic material to withstand the pressures created during aspiration and injection. The barrel wall is preferably extrusion molded from polypropylene, but other thermoplastic materials may be used as well.

The syringe is preferably assembled by pushing the piston completely into the barrel and inserting the plunger into the barrel. The plunger 80 is then forced against the piston 60 until the mushroom-shaped head 81 of the plunger snaps into the piston immediately behind the hook-shaped ends of the drag arms 62. A circumferential crimp 100 is then provided in the barrel wall 12. The location of the crimp is selected such that it limits the maximum volume of liquid which can be aspirated. Changing the location of the crimp 100 allows syringes of the same construction and dimensions being for a range of standard injection volumes.

What is claimed is:

1. An auto-destruct syringe, comprising a syringe barrel (12) for holding a fluid having an open rear end (14) and a closed front end (20) and a passage (23) extending through the closed end of the barrel to permit expulsion of fluid from the interior of the barrel, a piston assembly (50) reciprocatable in the barrel (12) and sealingly engaging the barrel wall, a plunger (80) having a forward portion normally positioned in the barrel (12) and a rearward portion to be manipulated by a user of the syringe, characterized in that the syringe further comprises a deforming mechanism (90) on one of the piston assembly (50) and the plunger (80) for permanently deforming the barrel wall, the deforming mechanism being movable from an at rest position wherein the barrel wall is not deformed by the deforming mechanism to a barrel wall engaging position wherein the barrel wall is permanently deformed by the deforming mechanism;

engaging means (87) mounted to the other of the piston assembly (50) and the plunger (80) for forcing the deforming mechanism (90) into the barrel wall engaging position upon rearward movement of the piston assembly; and a connecting structure for connecting the piston assembly (50) with the plunger (80), the connecting structure including a first coupling mechanism (62, 81) for allowing the piston assembly (50) to be moved rearward by pulling back the plunger during an initial aspiration stroke without engagement of the engaging means with the deforming mechanism, and a second coupling mechanism (64, 81) for coupling the piston assembly (50) with the plunger (80) during a second aspiration stroke such that the engaging means (87) engages the deforming mechanism (90).

2. An auto-destruct syringe as defined in claim 1, characterized in that the first coupling mechanism includes a drag arm (62) of the piston assembly (50) having a hook-shaped portion (63) for engagement by an enlarged head (81) of the plunger (80), the hook-shaped portion (63) being positioned on the drag arm (62) such that the engaging means (87) does not force the deforming mechanism (90) into the barrel wall when the hook-shaped portion (63) is engaged by the plunger head (81), and the second coupling mechanism includes a carrier arm (64) of the piston assembly (50) having a hook-shaped portion (68) for engagement by the plunger head (81), the hook-shaped portion (68) being positioned on the carrier arm (64) such that it is only engaged by the plunger head (81) after an injection stroke, whereby when the plunger head (81) engages the hook-shaped portion (68), the engaging means (87) forces the deforming mechanism (90) into the barrel wall.

3. An auto-destruct syringe as defined in claim 1 or 2, characterized in that the deforming mechanism (90) is mounted on the piston assembly (50) and the engaging means (87) is mounted on the plunger (80).

4. An auto-destruct syringe as defined in claim 3, characterized in that the deforming mechanism (90) includes a pair of deforming elements (66) which are radially outwardly protruding from a pair of spaced apart carrier arms (64) integral with the piston assembly (50) and the engaging means (87) is a ramp portion (87) provided on a front end (81) of the plunger which ramp portion progressively forces the carrier arms (64), and the associated deforming elements (66), radially outwardly during engagement therewith when the plunger is moved rearward relative to the piston assembly (50) and the plunger head (81) engages the hook-shaped portion (68).

5. An auto-destruct syringe as defined in claim 4, characterized in that the hook portions (68) are integral with the carrier arms (64) and ride up on the ramp portion (87) when the plunger (80) is pulled back relative to the piston assembly (50), thereby forcing the deforming elements (66) into the barrel wall.

6. An auto-destruct syringe as defined in claim 5, characterized in that the coupling mechanism includes a pair of drag arms (62) integral with the piston assembly (50) and an alternately positioned pair of carrier arms (64), the drag arms (62) each having a hook-shaped rear end (63) for coupling engagement with the plunger head (81).

7. An auto-destruct syringe as defined in claim 1, characterized in that the piston assembly (50) includes a seal (52) fitted onto the piston (60), the seal being made of material and size to sealingly fit into the barrel 12), the piston (60) including a cylindrical base (61) to which the drag arms (62) and carrier arms (64) are mounted, and that plunger (80) has a substantially mushroom-shaped, enlarged head (81) for engagement with the hook-shaped portions (63. 68) of the drag arms (62) and carrier arms (64) respectively, and a frusto-conical ramp portion (68) behind the plunger head (81), the ramp portion increasing in diameter towards the plunger head (81) for pushing the carrier arms radially outwardly during the second aspiration stroke.

8. An auto-destruct syringe as defined in claim 1, characterized in that a stop (100) is provided for preventing removal of the plunger (80) from the barrel.

9. An auto-destruct syringe as defined in claim 8, characterized in that the stop (100) is a circumferential, radially inwardly extending crimp in the barrel wall.

10. An auto-destruct-syringe as defined in claim 1, characterized in that the syringe barrel has an even wall thickness of 0.01 to 0.2 mm and is extruded of a substantially rigid thermoplastic material able to withstand the pressures created during aspiration and injection of the syringe whereby the small thickness of the barrel wall ensures reliable deformation of the barrel wall by the deforming, means independent of the speed of and force applied to the plunger (80) during the second aspiration stroke.

* * * * *